(12) United States Patent
Choi et al.

(10) Patent No.: US 8,025,900 B2
(45) Date of Patent: Sep. 27, 2011

(54) SUSTAINED RELEASE COMPOSITION OF PROTEIN DRUG

(75) Inventors: Suk Young Choi, Daejeon (KR); Hoon Sung Jeh, Daejeon (KR)

(73) Assignee: LG Life Science, Ltd. (KR)

( * ) Notice: Subject to any disclaimer, the term of this patent is extended or adjusted under 35 U.S.C. 154(b) by 1071 days.

(21) Appl. No.: 11/816,744

(22) PCT Filed: Feb. 21, 2006

(86) PCT No.: PCT/KR2006/000571
§ 371 (c)(1),
(2), (4) Date: Aug. 21, 2007

(87) PCT Pub. No.: WO2006/088336
PCT Pub. Date: Aug. 24, 2006

(65) Prior Publication Data
US 2008/0260654 A1      Oct. 23, 2008

(30) Foreign Application Priority Data

Feb. 21, 2005   (KR) .................. 10-2005-0014051

(51) Int. Cl.
*A61K 9/22*        (2006.01)
*A61K 9/14*        (2006.01)
*A61K 38/21*       (2006.01)
*A61K 38/18*       (2006.01)

(52) U.S. Cl. ........ 424/468; 424/485; 424/85.4; 514/737

(58) Field of Classification Search .................. 424/468, 424/485, 85.4; 514/7.7
See application file for complete search history.

(56) References Cited

U.S. PATENT DOCUMENTS

| | | | |
|---|---|---|---|
| 4,041,155 A | 8/1977 | Fenichel et al. | |
| 4,278,661 A * | 7/1981 | Knight, Jr. ................ | 424/85.6 |
| 5,385,738 A | 1/1995 | Yamahira et al. | |
| 5,416,071 A | 5/1995 | Igari et al. | |
| 6,004,549 A | 12/1999 | Reichert et al. | |
| 6,011,011 A | 1/2000 | Hageman | |
| 6,375,989 B1 | 4/2002 | Badylak et al. | |
| 2003/0064105 A1 | 4/2003 | Kim et al. | |

FOREIGN PATENT DOCUMENTS

| | | |
|---|---|---|
| JP | 01287041 | 11/1989 |
| WO | 9406452 | 3/1994 |
| WO | 9618417 | 6/1996 |
| WO | 0128524 | 4/2001 |

OTHER PUBLICATIONS

Handbook of Pharmaceutical Excipients; Ainley Wade, Paul J. Weller, 1994.
Instability, stabilization, and formulation of liquid protein pharmaceuticals, Wei Wang, Int'l Journal of Pharmaceutics, 185 (1999) 129-188.
Quantikine IVD, Human EPO Immunoassay, R&D Systems Mfg. Package Insert.
Interferon Alfa-2 Concentrated Solution, European Pharmacopoeia 5.0. Jan. 2005:0836.
Convenient Assay for Interferons, Journal of Virology, Feb. 1981, p. 755-758.
International Search Report, PCT/KR2006/000571, Apr. 14, 2006.
International Preliminary Report on Patentability, PCT/KR2006/000571, Jun. 4, 2007.
Written Opinion, PCT/KR2006/000571, Apr. 14, 2006.

* cited by examiner

*Primary Examiner* — Johann Richter
*Assistant Examiner* — Abigail Fisher
(74) *Attorney, Agent, or Firm* — Cantor Colburn LLP (57) ABSTRACT

Disclosed is a sustained release composition of a protein drug. The composition comprises a carrier substrate and a protein drug incorporated in the carrier substrate. The carrier substrate is consisting essentially of a hyaluronic acid or its salts, an amino acid, and a polyalkyl oxide.

19 Claims, 6 Drawing Sheets

SUSTAINED RELEASE COMPOSITION OF PROTEIN DRUG

BACKGROUND OF THE INVENTION

1. Field of the Invention

This invention relates to a sustained-release composition comprising a physiologically active protein drug, a hyaluronic acid or salts thereof, a polyalkyl oxide, and an amino acid. The composition allows a persistent release of the physiologically active drug for an extended period of time, preferably for one week or longer.

2. Description of the Related Art

It has been reported that protein drugs are useful for treating various disease because they have a high physiological activity in the living body and a high specificity to a target. It is also reported that protein drugs have a short half-life and a low absorption rate in the living body, which limit the availability of protein drugs as a treatment drug. Protein drugs are usually administered to a patient via injection routes. The injection of protein drugs into the patient is usually painful. The half life of the injected protein drugs in the patient is generally 2-4 hours and the patients are required to be administered with the drugs everyday or every other day for an extended period of time, for example, one year or longer.

Sustained release formulations of protein drugs were proposed. During the early stage of the development of sustained release formulations of a protein drug, liposomes, microcapsules, and implants containing the drug have been suggested. However, these formulations were not satisfactory because the protein contained in the formulations easily lost its activity and they failed to produce a sustained release of the drug. Polymer microparticles containing a protein drug have been proposed. The microparticles formed from a non-biodegradable polymer have problems that they are not digested in the patient's body, and thus sometimes, an operation to remove the unsolved residues was needed. They are also harmful to the living body and the control of the release of the drug is difficult.

In order to overcome the drawbacks related with the use of a non-biodegradable polymer, microparticles in which a drug is entrapped into the biodegradable polymer have been suggested. The biodegradable polymer of the microparticles is slowly degraded in patient's body and the drug is released. As biodegradable and biocompatible polymers, synthetic polyesters such as polylactides, polyglycolides, poly(lactide-co-glycolide) (PLGA), polyanhydrides, polyorthoesters, polyphosphazenes, pseudopolyaminoacids have been employed. Microcapsules made from polyesters such as PLGA produce a sustained release of a peptide drug for an extended period of time ranging from one week to one month. However, the use of the PLGA in producing sustained release formulations of protein drug was limited because the hydrophobic property of the PLGA caused the degeneration of protein drugs, which destroys the physiological activity of the drug. The degradation of the PLGA itself in the patient body, which generates an acid and thus reduces the pH of the microparticles, also accelerates the degeneration and aggregation of the protein drug. The use of organic solvents, which are commonly employed in the production of microparticles using hydrophobic polymers, also causes unstabilization of the protein drug. The relatively slow digestion of the polymer in the patient also causes a feeling of a foreign substance.

A use of sustained release formulations made from a natural polymer has been proposed. Natural polymers such as gelatin, collagen, chitosan, carboxymethyl cellulose, alginate, or hyaluronic acids form a viscous gel upon absorbing water. The gel of the natural polymer produces a sustained release of a drug, including a protein drug. However, the gel easily loses its ability to retain the drug, when introduced into a patient body because the viscosity and density of the gel fast decreased in the patient body due to the digestion of the polymer and the dilution of gel inside the body. Thus, the natural polymer gel does not provide a satisfactory sustained release.

Hyaluronic acid is a natural, biodegradable, high molecular polymer made of N-acetyl-D-glucosamine and D-glucuronic acid. It is found in various organs and tissues in the living body. It is used in eye operations and rheumatisms treatments. There have been attempts to use hyaluronic acid gels in sustained release formulations. Generally, the higher the viscosity of the hyaluronic acid gel, the more effective in producing the sustained release of a protein drug. However, a composition containing several % of the hyaluronic acid gel is too viscous and difficult to be introduced into a patient by an injection.

Like other natural polymer gel formulations, hyaluronic acid gel formulation of a protein drug does not provide an effective sustained release of the drug once it is introduced into a subject. For example, when an insulin formulation comprising 1% hyaluronic acid gel, as disclosed in JP 1989-287041, was injected to a rabbit, the glucose blood level lowering effect lasted not more than 24 hours after the injection. U.S. Pat. No. 5,416,071 describes a sustained release formulation of interferon comprising 1.5% hyaluronic acid and plasma protein. When the formulation of interferon was introduced into a subject, the blood level of interferon sharply decreased to $\frac{1}{10}$ of its initial level, within 24 hours after the injection.

As an alternative to gel formulations, microparticles comprising a protein drug and a hyaluronic acid or its salts, which are produced by spray drying, have been proposed. For example, U.S. Application Publication No. 2003/0064105 describes a sustained release formulation which was prepared by producing hyaluronic acid microparticles comprising a protein drug using spray drying; coating the microparticles with a lipophilic material such as lecithin, and dispersing the coated microparticles into an oil. It also describes that the coated microparticles are formulated into an oil-in-water emulsion. When an oil-in-water emulsion of the lecithin-coated microparticles of interferon-alpha was injected to a rabbit, the blood level of the interferon-alpha was maintained for an extended period of time.

To eliminate the coating process mentioned above, a lipophilic material can be dispersed in a solution containing a hyaluronic acid and an active ingredient and the resulting solution is subject to drying (e.g., spray drying). U.S. Application Publication No. 2003/0064105. For a practical viewpoint of commercialization, the solubilization of the lipophilic material is cumbersome as well as the quantization of the drug content and the analysis of the microparticles are difficult.

U.S. Pat. No. 6,375,988 discloses a drug composition with a controlled drug release rate. The drug composition comprises: a matrix formed of (a) a biodegradable, biocompatible high-molecular substance and/or polyvalent metal ions or polyvalent metal ion source, and (b) hyaluronic acid or a salt thereof, and a drug incorporated as an ingredient (c) in the matrix. The component (a) includes gelatin, sodium casein, albumin, lysozyme chloride, poly-L-lysine, chitosan, $Ca^{2+}$, $Al^{3+}$, and $Fe^{3+}$. The drug covers a broad spectrum from anti-inflammatory drugs to arthritis therapeutics. The hyaluronic acid or its salts have a molecular weight ranging from 600,000 to 2,000,000 Da, especially from 1,000,000 to 2,000,000 Da.

It does not specifically teach a controlled delivery of protein drugs. U.S. Pat. No. 6,375,988 does not teach a sustained release composition comprising a carrier substrate essentially consisting of a hyaluronic acid or its salts, an amino acid and a polyalkylene oxide and a protein drug incorporated in the carrier substrate, wherein a ratio of a molecular weight (Da) of the protein drug to a molecular weight (Da) of the polyalkylene oxide is about 1:0.5-1:10.

In conclusion, there still is a need for a sustained release formulation of a protein drug, which shows an excellent sustained release of the drug for an extended period of time while retaining the physiological activity of the drug.

Polyethylene glycol (PEG) is one type of polyalkyl oxides. Low molecular weight PEGs (molecular weight of less than 1000 Da) are liquid at the room temperature, while high molecular weight PEGs (molecular weight of 1000 Da or more) are solid. High molecular weight PEGs have been used as a plasticizer, a suppository base, and a hydrophilic excipient. Handbook of Pharmaceutical Excipients, $2^{nd}$ Ed., The Pharmaceutical Press (1994). Low molecular weight PEGs have mainly been used as a solvent or a vehicle for drug compositions. Low molecular weight PEGs have been used as a stabilizer to prevent crystallization or precipitation of protein drugs in liquid formulations of the protein drugs. International Journal of Pharmaceutics, 185, 129-188 (1999).

Low molecular weight PEGs in a liquid form were proposed to be used as a vehicle for a solid formulation of proteins. For example, U.S. Pat. No. 5,385,738 describes a method in which proteins such as IGF-1 or B-hGH mixed with collagen are freeze-dried and pulverized to give powders, which are then dispersed in the liquid PEG. U.S. Pat. No. 6,004,549 describes a use of PEGs as a vehicle of crystalline interferons. According to U.S. Pat. No. 6,004,549, mixtures of PEGs of different molecular weights are proposed. For example, it describes the use of the mixture of PEG 3350 and PEG 400 or PEG 40,000 and PEG 550 in the production of an injectable sustained release composition of crystalline interferons. Uses of the PEGs of molecular weight of 8000 Da or 3350 Da are also suggested. However, U.S. Pat. No. 6,004,549 does not teach or disclose a sustained release composition comprising a carrier substrate which consists essentially of a hyaluronic acid or its salts, an amino acid and a polyalkylene oxide and a protein drug incorporated in the carrier substrate, wherein a ratio of a molecular weight (Da) of the protein drug to a molecular weight (Da) of the polyalkylene oxide is about 1:0.5-1:10. The sustained release composition of interferon-alpha taught by U.S. Pat. No. 6,004,549 released interferon-alpha up to 48 hours after the injection.

It has been reported that drug compositions comprising low molecular PEGs as a vehicle produces a sustained release of a drug for a short period of time. For example, U.S. Pat. No. 4,041,155 describes a use of a solution of 80% PEG 400 or PEG 300 as a vehicle of somatostatin. A solution of somatostatin dispersed in a 38% PEG 400 solution showed a sustained release of somatostatin for 4 hours. U.S. Pat. No. 6,011,011 discloses a sustained release of protein drugs from a composition comprising PEG 300 or PEG 600. It was recommended to use less than 30% of PEG 300 because a high concentration of 40% by volume or more of PEG 300 may induce hemolytic effects around the injected site. Handbook of Pharmaceutical Excipients, $2^{nd}$, The Pharmaceutical Press (1994).

SUMMARY OF THE INVENTION

A composition comprising a carrier substrate and a protein drug incorporated into the carrier substrate, said carrier substrate consisting essentially of (a) a hyaluronic acid or its salts, (b) a polyalkyl oxide, and (c) an amino acid, wherein a ratio of a molecular weight (Da) of the protein drug to a molecular weight (Da) of the polyalkyl oxide is about 1:0.5-1:10.

The present invention is related to a sustained-release composition comprising a carrier substrate and a physiologically active protein drug incorporated into the carrier substrate, wherein the carrier substrate consists essentially of a hyaluronic acid or salts thereof in an amount sufficient to produce sustained release of the protein drug, a polyalkyl oxide in an amount sufficient to produce sustained release of the protein drug, and an amino acid in an amount sufficient to produce sustained release of the protein drug.

In the composition of the present invention, a ratio of a molecular weight (Da) of the protein drug to a molecular weight (Da) of the polyalkyl oxide is about 1:0.5-1:10. The composition preferably produces a sustained release of a protein drug at its effective amount or higher, for at least 7 days. Preferably, the carrier substrate and the protein drug can be formed into a microparticle. The microparticle may have an average diameter of 1-500 µm.

BRIEF DESCRIPTION OF THE INVENTION

DETAILED DESCRIPTION OF THE INVENTION

The carrier substrate contained in the sustained release composition of the present invention consists essentially of a hyaluronic acid or its salts, a polyalkyl oxide, and an amino acid.

The term "carrier substrate," as employed herein, indicates a base material or a matrix which allows an entrapment and a sustained release of a drug. The carrier substrate may account for about 50-99.95% by weight, and preferably about 70-99.95% by weight, based on the dry weight of the composition.

According to the present invention, physical interaction or van der Waals interaction between the hyaluronic acid or its salts, the amino acid, and the polyalkyl oxide renders the formation of the carrier substrate. A dense structure or a dense texture of microparticles formed from a hyaluronic acid or its salts, an amino acid and a polyalkyl oxide allows the production of the sustained release of a protein drug incorporated therein for an extended period of time. The microparticles may have cross-linked bonds or chemical bonds formed among each of ingredients. In this case, if necessary, a cross-linking agent may be used. The cross-linking agent is known to one skilled in the art.

The term "consists essentially of," as employed herein, means that the carrier substrate contains, as essential ingredients, a hyaluronic acid or its salts, a polyalkyl oxide and an amino acid. The carrier substrate may contain other non-essential ingredients which do not materially effect its sustained releasing effect.

A hyaluronic acid, which may be used in the present invention, may be a free acid or salts. The salts may include, but not be limited to, sodium hyaluronate, potassium hyaluronate, ammonium hyaluronate, calcium hyaluronate, magnesium hyaluronate, zinc hyaluronate, and cobalt hyaluronate. Sodium hyaluronate may be preferably used. Hyaluronic acid or salts may be used in single or as mixtures.

Various methods of extraction, purification, and measurement may be used to produce hyaluronic acids of various molecular weights. Hyaluronic acids or salts thereof, which are used in the present invention, may have a molecular weight of 1,000,000 Da or more, and preferably 3,000,000 Da or more. There is no upper limit to the molecular weight of the hyaluronic acids or salts thereof, but currently hyaluronic acids of up to 4,000,000-6,000,000 Da are commercially available.

A hyaluronic acid or its salts may be incorporated into the composition of the present invention in an amount of 5-90% by weight, preferably 10-60% by weight, and more preferably 20-50% by weight, based on the dry weight of the composition. In one embodiment of the present invention, the composition of the invention comprises sodium hyaluronate of the molecular weight of about 3,000,000 Da in an amount of 20-50% by weight based on the dry weight of the composition.

The term "dry weight," as employed herein, means a weight of solids obtained by removing liquids from the composition by, for example, evaporation or filtration.

The term "polyalkyl oxide," as used in the present application, includes polyalkyl oxides and polyalkylene oxides. They may be exemplified by, but not limited to, polyethylene glycol (PEG), polypropylene glycol, and a copolymer of polyethylene and polypropylene glycol (e.g., poloxamers). They may be used in single or as mixtures. Polyalkyl oxide is preferably polyethylene glycol.

As discussed above, PEGs have been used in pharmaceutical compositions, particularly sustained release compositions. However, it was not reported that the use of a polyalkyl oxide, particularly polyethylene glycol, having a molecular weight similar to or larger than that of a protein drug, in combination with a hyaluronic acid and an amino acid enhances the sustained release of the protein drug. The ratio of molecular weights of the protein drug to the polyalkyl oxide is generally in the range of about 1:0.5-1:10, preferably about 1:0.8-1:5, and more preferably about 1:1. When PEG 8000, PEG 20,000, and PEG 35,000 each were employed in sustained release compositions of interferon-alpha (M.W. 20,000 Da), the blood level of interferon-alpha of the compositions were maintained 100 pg/ml for more than 5 days. (Examples 3-5) In particular, the composition of Example 4 employing PEG 20,000 showed the longest sustained-release effects.

A polyalkyl oxide may be incorporated into the composition of the present invention in an amount of 1-90% by weight, preferably 5-60% by weight, and more preferably 10-40% by weight, based on the dry weight of the composition.

An amino acid has been used as a stabilizer of proteins, in single or as mixtures with other known pharmaceutical excipient. International Journal of Pharmaceuticals, 185, 129-188 (1999). In the present invention, amino acid is one of the components of the carrier substrate and may be employed in an amount of about 5% by weight or more, preferably about 10-80% by weight or more, and more preferably about 20-60% by weight, based on the dry weight of the composition.

According to the present invention, hydrophobic amino acids are preferably used to enhance the sustained release of the protein drug. (See Experimental Example 5.) The term "hydrophobic amino acids" as employed in the present application may include aspartic acid, asparagines, histidine, isoleucine, leucine, methionine, phenylalanine, serine, tryptophan, tyrosine, or valine. Isoleucine, leucine, methionine, or valine may be advantageously used. Leucine is particularly preferred. Amino acids may have one or more substituents as long as the substitution does not adversely affect the hydrophobicity or the sustained release profile of the composition. Amino acids may be used in single or as mixtures.

When used together, each in appropriate amounts, a hyaluronic acid or salts thereof, a polyalkyl oxide, and an amino acid produce an enhanced sustained release of protein drugs, compared when they are used individually or as mixtures of two ingredients. (See Experiment Example 2) The total amount of the hyaluronic acid or its salts, the polyalkyl oxide and the amino acid may be in the range of about 50-99.95% by weight, and preferably about 70-99.95% based on the dry weight of the composition.

In one embodiment, the composition of the present invention comprises a carrier substance which consists essentially of sodium hyaluronate with a molecular weight of about 3,000,000 Da in an amount of 20-50% by weight based on the dry weight of a composition, a polyethylene glycol having a molecular weight which is approximately the same as that of a protein drug contained in the composition in an amount of 10-40% by weight based on the dry weight of a composition, and a hydrophobic amino acid such as leucine in an amount of 20-60% by weight based on the dry weight of a composition; and a protein drug in an amount of 0.05-5% by weight based on the dry weight of a composition.

The composition of the present invention comprises a physiologically active protein drug. The term "a physiologically active protein drug" as employed in the present application indicates proteins or (poly)peptides which exhibit antagonistic effects on various physiological phenomena and exist in active form.

Examples of the protein drug, which can be used in the composition of the present invention include, but not be limited to, human growth hormones, bovine growth hormones, porcine growth hormones, growth hormone release hormones, growth hormone release peptides, interferons and interferon receptors (e.g., interferon-alpha, -beta and -gamma, Type I soluble interferon receptor), granulocyte-colony stimulating factors (G-CSFs), granulocyte-macrophage-colony stimulating factors (GM-CSFs), glucagons-like peptides (GLP-1 and the like), bone morphogenesis proteins, follicle stimulating hormones, exendins, G-protein-coupled receptors, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, -28, -29, -30 and the like), interleukin receptors (e.g., IL-1 receptor, IL-4 receptor and the like), enzymes (e.g., glucocerebrosidase, iduronate-2-sulfatase, alpha-galactosidase-A, agalsidase alpha, beta- or alpha-L-iduronidase, butyrylcholinesterase, chitinase, glutamate decarboxylase, imiglucerase, lipase, uricase, platelet-activating factor acetylhydrolase, neutral endopeptidase, myeloperoxidase and the like), linterleukin- or cytokine-binding proteins (e.g., IL-18bp, TNF-binding proteins), macrophage activating factors, macrophage peptides, B cell factors, T cell factors, protein A, allergy inhibitors, cell necrosis glycoprotein, immune toxins, lymph toxins, tumor necrosis factors, tumor suppressing factors, transitional growth factors, alpha-1 antitrypsin, albumin, alpha-lactalbumin, apolipoprotein-E, erythropoietin, highly glycosylated erythropoietin, angiopoietin, hemoglobin, thrombin, thrombin receptor activating peptides, thrombomodulin, blood factor VII, blood factor VIIa, blood factor VIII, blood factor IX, blood factor XIII, plasminogen activating factor, fibrin-binding peptides, urokinases, streptokinases, hirudin, protein C, C-reactive proteins, rennin inhibitors, collagenase inhibitors, superoxide dismutases, leptin, platelet-originated growth factor, epithelial growth factor, epidermal growth factor, angiostatin, angiotensin, myelophoiesis growth factor, myelophoiesis stimulating factor, calcitonin, insulin, atriopeptin, cartilage inducer, elcatonin, joint tissue activating factor, tissue factor pathway inhibitor, follicle stimulating hormone, progesterone forming hormone, progesterone forming hormone releasing hormone, nerve growth factors (e.g., nerve growth factor, cilliary neurotrophic factor, axogenesis factor-1, brain-natriuretic peptide, glial derived neurotrophic factor, netrin, neurophil inhibitor factor, neurotrophic factor, neuturin and the like), parathormone, relaxin, cycretin, somatomedine, insulin-like growth factor, adrenocortical hormones, glucagons, cholecystokynine, pancreatic polypeptides, gastrin releasing peptide, corticotropin releasing factor, thyroid stimulating hormone, autotaxin, lactoferrin, myostatin, receptors (e.g., TNFR(P75), TNFR(P55), IL-1 receptor, VEGF receptor, B cell activating factor receptor and the like), receptor antagonists (e.g., IL1-Ra and the like), cell surface antigens (e.g., CD 2, 3, 4, 5, 7, 11a, 11b, 18, 19, 20, 23, 25, 33, 38, 40, 45, 69 and the like), virus vaccine antigens, monoclonal antibodies, polyclonal antibodies, antibody fragments (e.g., scFv, Fab, Fab', $F(ab')_2$ and Fd), virus-originated vaccine antigens, growth factors (e.g. EGF, PDGF, FGF and the like), antibody-fusion protein, antibody-fragment fusion protein, and the like.

Protein drugs which require a frequent administration into a patient, such as interferons, erythropoietin, granulocyte-colony stimulating factor, and follicle-stimulating hormones (FSHs), may be advantageously employed in the present application. Sustained release compositions containing one of these protein drugs, which are prepared according to the present invention, produced sustained release of the protein drug at its effective serum level for more than 7 days. (Experimental Examples 7 and 8)

The term "effective serum level" or "effective concentration," as employed herein means a concentration of a drug in the blood of a subject, at or above which an intended physiological change in a biological system occurs. The values of effective serum level vary with the kind of the drug used and the subject.

The composition of the present invention, which comprises a carrier substrate and a protein drug incorporated in the carrier substrate may be produced by various known methods of producing a solid pharmaceutical compositions. For example, it may be produced in the form of a film, a pellet, a filament, a cylinder, or microparticle. If necessary, pharmaceutically acceptable excipients may be used for the production of the compositions. The types and the amounts of the pharmaceutically acceptable excipients are known to the one skilled in the art.

The composition is preferably formulated into microparticles. The microparticles may be in a spherical, a non-spherical or a irregular shape. The average sizes of the microparticle may be in the range from about 1 μm to about 500 μm. For the purpose of injection, the microparticles may preferably have an average size of about 100 μm or less.

Microparticles may be produced by various methods known to one skilled in the art. Freeze drying or spray drying may be employed. For example, an aqueous solution of a hyaluronic acid or its salts, an amino acid, and polyalkyl oxide is mixed with a solution of a protein drug, and the resulting mixture is subjected to freeze drying or spray drying to produce microparticles, in which the protein drug is incorporated into a carrier substrate. A homogeneous solution mixture of a protein drug, a hyaluronic acid or its salts, a polyalkyl oxide and an amino acid may be applied to a spray-dryer for evaporating water from the sprayed fine droplets of the homogenous solution. The dried microparticles have the same composition of the original solution, but the drug molecules are entrapped in the resulted microparticles.

Spray drying may preferably be used because it produces homogenous spherical microparticles, which are easily dispersed in a dispersant. Homogenous spherical microparticles are also easy to be administered into a subject by various injection methods such as subcutaneous, intramuscular, intraleseional or intravenous.

The term "incorporated" or "incorporated into a carrier substrate," as employed herein with respect to the structure of the composition of the present invention, means that a protein drug is entrapped into a resulted carrier substrate, which may, for example, preferably be in the form of microparticles. The term "entrapped" means that a molecule is confined in a three dimensional space by any means such as a carrier substrate matrix itself or ionic/nonionic bonding between the drug and the matrix.

The sustained release composition of the present invention may be administered via various routes. The term "administration," as employed herein, means an introduction or delivery of a certain material into a patient through various routes. Any routes may be used as long as they allow a delivery of a drug to a target tissue. For example, intraperitoneal, intraveneous, intramuscular, subcutaneous, intracutaneous, topical, intranasal, pulmonary, and rectal administration may be employed. Injectal administrations may be advantageously employed. Subcutaneous administration is preferred. The composition of the present invention also may be administered through other routes such as inhalational, endoscopial or laparoscopial routes.

The composition of the present invention may further comprise additional carriers depending on dosage forms or administration routes. A stabilizer of a protein drug may be used. The stabilizer may form a covalent bond or a coordinate bond with the protein drug, and include, but not be limited to, sugars such as sucrose, lactose, or glucose, polyols such as mannitol or glycerol, surfactants such as Tweens, lecithin, phosphates, and inorganic salts. The stabilizer may be used in single or as mixtures. It is within the skill of ordinary skilled in the art to determine the types and the amounts of the stabilizer.

The present inventors found that the compositions of interferon-alpha according to the present invention exhibit a sustained release for a longer extended period of time when they do not contain a stabilizer than when they contain a stabilizer. In one experiment using a composition comprising lecithin as a stabilizer and another composition without lecithin, both compositions produced sustained releases of interferon-alpha for more than 7 days. Interestingly, the composition without lecithin produced a longer sustained release. (Experimental Example 6)

This result is contrary to the teachings of publications in the art. For example, U.S. Application Publication 2003/0064105 describes a sustained release composition of hyaluronic acid microparticles, in which the microparticles are coated with a lipophilic material such as lecithin to enhance the dispersibility of the hyaluronic microparticles and consequently the sustained release.

The composition of the present invention may be administered by various injection routes. For this purpose, the composition may be dispersed into an injectable solution carrier. The injectable solution carrier may include, but not be limited to, an aqueous injection solution such as distilled water or injectable buffers; non-aqueous injection solution such as corn oil, sesame oil, cotton seed oil, soybean oil, peanut oil, mono-, di-, and tri-glyceride, mineral oil, squalene or mixtures thereof. If necessary, the injection formulation may further comprise a dispersant, an antiseptic agent, an anesthetic agent, a buffer, or a preservative.

The exact dose and regimen for administration of the composition will necessarily be dependent upon the needs of the individual subject being treated, the type of treatment, the administration routes, the age, the gender and the body weight of the individual subject, the degree of affliction or need and the judgment of the medical practitioner as well as the kind of the drug.

The present invention is illustrated further by the following examples, which are not to be construed as limiting the invention in scope or spirit to the specific procedures and compositions described in them.

EXAMPLE 1

Preparation of Microparticles of Interferon-alpha

A solution of interferon-alpha was prepared by dissolving interferon-alpha in 10 mM acetate buffer to a concentration of 1-2 mg/ml. Leucine (3 mg/ml), methionine (1.5 mg/ml), and PEG 20,000 (1.5 mg/ml) were dissolved in pure water. Sodium hyaluronate (MW 3,000,000 Da) (3 mg/ml) was dissolved into the resulting solution.

The interferon-alpha solution was added to the solution of leucine, methionine, PEG and sodium hyaluronate to a final concentration of 0.015 mg/ml to obtain a solution. The solution was introduced to a spray dryer (Mobile Minor™, Niro) at a rate of 20 ml/min to produce microparticles. The temperature of air at the inlet was 100° C. The diameters of the produced microparticles are between 2 μm and 200 μm.

EXAMPLE 2

Preparation of Microparticles of Interferon-alpha

A solution of interferon-alpha was prepared by dissolving interferon-alpha in 10 mM acetate buffer to a concentration of 1-2 mg/ml. Lecithin was hydrated with pure water to a concentration of 5 mg/ml and then passed through a microfluidizer (Microfluidizer®, Microfluidics Corporation) to produce a lecithin dispersion. The lecithin particles have a size ranging from 50 nm to 100 nm.

Leucine (3 mg/ml) and PEG 20,000 (1.5 mg/ml) were dissolved in pure water. Sodium hyaluronate with a molecular weight of 3,000,000 Da (3 mg/ml) was dissolved into the resulting solution.

The lecithin dispersion was added to the solution containing leucine, PEG 20,000 and sodium hyaluronate obtained above to a concentration of 0.525 mg/ml and mixed homogeneously. The interferon-alpha solution was added to a final concentration of 0.075 mg/ml to obtain a solution. The resulting solution was introduced to a spray dryer (Mobile Minor™, Niro) at a rate of 20 ml/min to produce microparticles. The temperature of air at the inlet was 100° C. The diameters of the produced microparticles are between 2 μm and 200 μm.

COMPARATIVE EXAMPLE 1

Preparation of Microparticles of Interferon-alpha without PEG and Amino Acid

A solution of interferon-alpha was prepared by dissolving interferon-alpha in 10 mM acetate buffer to a concentration of 1-2 mg/ml. Lecithin was hydrated with pure water to a concentration of 5 mg/ml and then passed through a microfluidizer (Microfluidizer®, Microfluidics Corporation) to produce a lecithin dispersion. The lecithin particles have a size ranging from 50 nm to 100 nm.

Sodium hyaluronate (molecular weight 3,000,000 Da) was dissolved in pure water to a concentration of 3 mg/ml. The lecithin dispersion was added to the sodium hyaluronate solution to a concentration of 0.51 mg/ml and mixed homogeneously. The interferon-alpha solution was added to a final concentration of 0.15 mg/ml to obtain a solution. The solution was introduced to a spray dryer (Mobile Minor™, Niro) at a rate of 20 ml/min to produce microparticles. The temperature of air at the inlet was 100° C. The diameters of the produced microparticles are between 2 μm and 200 μm.

COMPARATIVE EXAMPLE 2

Preparation of Microparticles of Interferon-alpha without PEG

A solution of interferon-alpha was prepared by dissolving interferon-alpha in 10 mM acetate buffer to a concentration of 1-2 mg/ml. Lecithin was hydrated with pure water to a concentration of 5 mg/ml and then passed through a microfluidizer (Microfluidizer®, Microfluidics Corporation) to produce a lecithin dispersion. The lecithin particles have a size ranging from 50 nm to 100 nm.

Leucine was dissolved in pure water to a concentration of 3 mg/ml, to which sodium hyaluronate (molecular weight 3,000,000 Da) was dissolved to a concentration of 3 mg/ml.

The lecithin dispersion was added to the solution containing leucine and sodium hyaluronate to a concentration of 0.5025 mg/ml and mixed homogeneously. The interferon-alpha solution was added to a final concentration of 0.075 mg/ml to obtain a solution. The solution was introduced to a spray dryer (Mobile Minor™, Niro) at a rate of 20 ml/min to produce microparticles. The temperature of air at the inlet was 100° C. The diameters of the produced microparticles are between 2 μm and 200 μm.

COMPARATIVE EXAMPLE 3

Preparation of Microparticles of Interferon-alpha without Amino Acid

A solution of interferon-alpha was prepared by dissolving interferon-alpha in 10 mM acetate buffer to a concentration of 1-2 mg/ml. Lecithin was hydrated with pure water to a concentration of 5 mg/ml and then passed through a microfluidizer (Microfluidizer®, Microfluidics Corporation) to produce a lecithin dispersion. The lecithin particles have a size ranging from 50 nm to 100 nm.

PEG 20,000 was dissolved in pure water to a concentration of 1.5 mg/ml, to which sodium hyaluronate (molecular weight 3,000,000 Da) was dissolved to a concentration of 3 mg/ml.

The lecithin dispersion was added to the solution containing PEG and sodium hyaluronate to a concentration of 0.5025 mg/ml and mixed homogeneously. The interferon-alpha solution was added to a final concentration of 0.075 mg/ml to obtain a solution. The solution was introduced to a spray dryer (Mobile Minor™, Niro) at a rate of 20 ml/min to produce microparticles. The temperature of air at the inlet was 100° C. The diameters of the produced microparticles are between 2 µm and 200 µm.

EXAMPLES 3-5

Preparation of Microparticles of Interferon-alpha with PEGs of Different Molecular Weights A solution of interferon-alpha was prepared by dissolving interferon-alpha in 10 mM acetate buffer to a concentration of 1-2 mg/ml. Lecithin was hydrated with pure water to a concentration of 5 mg/ml and then passed through a microfluidizer (Microfluidizer®, Microfluidics Corporation) to produce a lecithin dispersion. The lecithin particles have a size ranging from 50 nm to 100 nm.

Leucine and PEGs (molecular weights 8,000 (Example 3), 20,000 (Example 4), or 35,000 (Example 5)) were dissolved in pure water to concentrations as shown in Table 1 below. Sodium hyaluronate (molecular weight 3,000,000 Da) was dissolved into the resulting solution to the concentrations as shown in Table 1.

The lecithin dispersion was added to the solution containing leucine, PEG and sodium hyaluronate to a concentration of 0.5025 mg/ml and mixed homogeneously. The interferon-alpha solution was added to the final concentrations as shown in Table 1. The resulting solution was introduced to a spray dryer (Mobile Minor®, Niro) at a rate of 20 ml/min to produce microparticles. The temperature of air at the inlet was 100° C. The diameters of the produced microparticles are between 2 µm and 200 µm.

TABLE 1

(Unit: mg/ml)

| Example | Hyaluronic acid | Interferon-α | PEG MW (Da)/ conc. | L-Leucine | Lecithin |
|---------|-----------------|--------------|--------------------|-----------|----------|
| 3 | 3 | 0.075 | 8,000/1.5 | 3 | 0.5025 |
| 4 | 3 | 0.075 | 20,000/1.5 | 3 | 0.5025 |
| 5 | 3 | 0.075 | 35,000/1.5 | 3 | 0.5025 |

EXAMPLES 6-10

Preparation of Microparticles of Interferon-alpha with Various Amounts of PEGs

Lecithin was hydrated with pure water to a concentration of 5 mg/ml and then passed through a microfluidizer (Microfluidizer®, Microfluidics Corporation) to produce a lecithin dispersion. The lecithin particles have a size ranging from 50 nm to 100 nm. A solution of interferon-alpha was prepared by dissolving interferon-alpha in 10 mM acetate buffer to a concentration of 1-2 mg/ml.

Leucine and PEG 20,000 were dissolved in pure water to the concentrations as shown in Table 2 below. Sodium hyaluronate (molecular weight 3,000,000 Da) was dissolved into the resulting solution to the concentrations as shown in Table 2.

The lecithin dispersion was added to the solution containing leucine, PEG and sodium hyaluronate to the concentrations as shown in Table 2 and mixed homogeneously. The interferon-alpha solution was added to the final concentrations as shown in Table 2. The solution was introduced to a spray dryer (Mobile Minor™, Niro) at a rate of 20 ml/min to produce microparticles. The temperature of air at the inlet was 100° C. The diameters of the produced microparticles are between 2 µm and 200 µm.

TABLE 2

(Unit: mg/ml)

| Example | PEG (wt %)* | HA | Interferon-α | PEG | L-Leucine | Lecithin |
|---------|-------------|----|--------------|-----|-----------|----------|
| 6 | 4.4 | 3 | 0.015 | 0.3 | 3 | 0.5025 |
| 7 | 7.5 | 3 | 0.015 | 0.525 | 3 | 0.5025 |
| 8 | 10.3 | 3 | 0.015 | 0.75 | 3 | 0.5025 |
| 9 | 14.7 | 3 | 0.015 | 1.125 | 3 | 0.5025 |
| 10 | 18.7 | 3 | 0.015 | 1.5 | 3 | 0.5025 |

*The amounts of PEG is based on the dry weight of the composition.

EXAMPLES 11-14

Preparation of Microparticles of Interferon-alpha with Various Amino Acids

Lecithin was hydrated with pure water to a concentration of 5 mg/ml and then passed through a microfluidizer (Microfluidizer®, Microfluidics Corporation) to produce a lecithin dispersion. The lecithin particles have a size ranging from 50 nm to 100 nm. A solution of interferon-alpha was prepared by dissolving interferon-alpha in 10 mM acetate buffer to a concentration of 1-2 mg/ml.

Various amino acids as shown in Table 3 and PEG 20,000 were dissolved in pure water to the concentrations as shown in Table 3 below. Sodium hyaluronate (molecular weight 3,000,000 Da) was dissolved into the resulting solution to the concentrations as shown in Table 3.

The lecithin dispersion was added to the solution containing an amino acid, PEG and sodium hyaluronate to the concentrations a shown in Table 3 and mixed homogeneously. The interferon-alpha solution was added to the final concentrations as shown in Table 3. The solution was introduced to a spray dryer (Mobile Minor™, Niro) at a rate of 20 ml/min to produce microparticles. The temperature of air at the inlet was 100° C. The diameters of the produced microparticles are between 2 µm and 200 µm.

TABLE 3

(Unit: mg/ml)

| Example | Amino acid (Type/conc.) | HA | Interferon-α | PEG | Lecithin |
|---------|-------------------------|----|--------------|-----|----------|
| 11 | Histidine/3 | 3 | 0.075 | 1.5 | 0.5025 |
| 12 | Aspartic acid/3 | 3 | 0.075 | 1.5 | 0.5025 |
| 13 | Threonine/3 | 3 | 0.075 | 1.5 | 0.5025 |
| 14 | Methionine/3 | 3 | 0.075 | 1.5 | 0.5025 |

EXAMPLES 15-19

Preparation of Microparticles of Interferon-alpha

Lecithin was hydrated with pure water to a concentration of 5 mg/ml and then passed through a microfluidizer (Microfluidizer®, Microfluidics Corporation) to produce a lecithin dispersion. The lecithin particles have a size ranging from 50 nm to 100 nm. A solution of interferon-alpha was prepared by dissolving interferon-alpha in 10 mM acetate buffer to a concentration of 1-2 mg/ml.

An amino acid (leucine or methionine) and PEG 20,000 were dissolved in pure water to the concentrations as shown in Table 4. Sodium hyaluronate (molecular weight 3,000,000 Da) was dissolved into the resulting solution to the concentrations as shown in Table 4.

The lecithin dispersion was added to the solution containing an amino acid, PEG and sodium hyaluronate to the concentrations as shown in Table 4 and mixed homogeneously. The interferon-alpha solution was added to the final concentrations as shown in Table 4. The resulting solution was introduced to a spray dryer (Mobile Minor™, Niro) at a rate of 20 ml/min to produce microparticles. The temperature of air at the inlet was 100° C. The diameters of the produced microparticles are between 2 μm and 200 μm. Table 4 shows the amounts of each ingredient of the microparticles obtained, based on the dry weight of the microparticles.

TABLE 4

(Unit: wt %)

| Example | HA | Interferon-α | PEG | Leucine | Methionine | Lecithin |
|---------|------|--------------|------|---------|------------|----------|
| 15*     | 42.7 | 0.14         | 14.3 | 35.7    | 7.16       | 0        |
| 16      | 33.2 | 0.17         | 16.7 | 33.2    | 16.73      | 0        |
| 17      | 37.1 | 0.93         | 18.6 | 37.1    | 0          | 6.27     |
| 18      | 38.6 | 0.2          | 19.8 | 38.6    | 0          | 2.8      |
| 19      | 37.5 | 0.1          | 18.7 | 28      | 9.4        | 6.3      |

*In Example 15, isoleucine was employed instead of leucine.

EXAMPLE 20

Preparation of Microparticles of Erythropoietin

Lecithin was hydrated with pure water to a concentration of 5 mg/ml and then passed through a microfluidizer (Microfluidizer®, Microfluidics Corporation) to produce a lecithin dispersion. The lecithin particles have a size ranging from 50 nm to 100 nm. A solution of human recombinant erythropoietin was prepared by dissolving human recombinant erythropoietin in 10 mM acetate buffer to a concentration of 1-2 mg/ml.

Leucine and PEG 20,000 were dissolved in pure water to the concentrations of 3 mg/ml and 1.5 mg/ml, respectively. Sodium hyaluronate (molecular weight 3,000,000 Da) was dissolved into the resulting solution to the concentration of 3 mg/ml.

The lecithin dispersion was added to the solution containing leucine, PEG and sodium hyaluronate to the concentration of 0.525 mg/ml and mixed homogeneously. The human recombinant erythropoietin solution was added to the concentration of 0.075 mg/ml. The resulting solution was introduced to a spray dryer (Mobile Minor™, Niro) at a rate of 20 ml/min to produce microparticles. The temperature of air at the inlet was 100° C. The diameters of the produced microparticles are between 2 μm and 200 μm.

EXAMPLE 21

Preparation of Microparticles of Follicle-stimulating Hormone (FSH)

Lecithin was hydrated with pure water to a concentration of 5 mg/ml and then passed through a microfluidizer (Microfluidizer®, Microfluidics Corporation) to produce a lecithin dispersion. The lecithin particles have a size ranging from 50 nm to 100 nm.

Leucine and PEG 35,000 were dissolved in pure water to the concentrations of 3 mg/ml and 1.5 mg/ml, respectively. Sodium hyaluronate (molecular weight 3,000,000 Da) was dissolved into the resulting solution to the concentration of 3 mg/ml.

The lecithin dispersion was added to the solution containing leucine, PEG and sodium hyaluronate to the concentration of 0.51 mg/ml and mixed homogeneously. A urine-derived FSH (MW 40,000) was added to the concentration of 0.01 mg/ml. The resulting solution was introduced to a spray dryer (Mobile Minor™, Niro) at a rate of 20 ml/min to produce microparticles. The temperature of air at the inlet was 100° C. The diameters of the produced microparticles are between 2 μm and 200 μm.

EXAMPLE 22

Preparation of Microparticles of Erythropoietin

A solution of human recombinant erythropoietin was prepared by dissolving human recombinant erythropoietin in 10 mM acetate buffer to a concentration of 1-2 mg/ml.

Leucine, methionine, and PEG 20,000 were dissolved in pure water to the concentrations of 3 mg/ml, 1.5 mg/ml, and 1.5 mg/ml, respectively. Sodium hyaluronate (molecular weight 3,000,000 Da) was dissolved into the resulting solution to the concentration of 3 mg/ml.

The human recombinant erythropoietin solution obtained above was added to the solution of leucine, methionine and PEG 20,000 to the concentration of 0.015 mg/ml. The final solution was introduced to a spray dryer (Mobile Minor™, Niro) at a rate of 20 ml/min to produce microparticles. The temperature of air at the inlet was 100° C. The diameters of the produced microparticles are between 2 μm and 200 μm.

EXAMPLE 23

Preparation of Microparticles of Follicle-stimulating Hormone (FSH)

Leucine, methionine, and PEG 35,000 were dissolved in pure water to the concentrations of 3 mg/ml, 1.5 mg/ml and 1.5 mg/ml, respectively. Sodium hyaluronate (molecular weight 3,000,000 Da) was dissolved into the resulting solution to the concentration of 3 mg/ml.

To the solution containing leucine, methionine, PEG, and sodium hyaluronate, human recombinant FSH (MW about 40,000) was added to the concentration of 0.015 mg/ml. The final solution was introduced to a spray dryer (Mobile Minor™, Niro) at a rate of 20 ml/min to produce microparticles. The temperature of air at the inlet was 100° C. The diameters of the produced microparticles are between 2 μm and 200 μm.

EXPERIMENTAL EXAMPLE 1

Sustained Releases of Microparticles of the Invention

Microparticles of interferon-alpha were tested for their sustained release of interferon-alpha by using rats. Microparticles of interferon-alpha of Example 1 or Comparative Example 1 were dispersed into a medium chain triglyceride (MCT) (Myglyol 812, Sasol) to a concentration of 336 μg IFNα/ml to give injection dispersions. A 10 mM acetate buffer comprising interferon-alpha (24 µg/ml) was used as a control.

Each of the microparticle dispersions and the control (0.5 ml) were subcutaneously injected to Sprague Dawley rats (male, 7-8 weeks old). Blood samples were collected 8 hours after the injection and then on a daily basis for a week. Serum was separated from blood samples and the blood levels of interferon-alpha were measured using Enzyme-linked Immunoabsorbent Assay (ELISA) (Biotrak ELISA System (RPN 2789), Amersham Biosciences).

Figure 1:
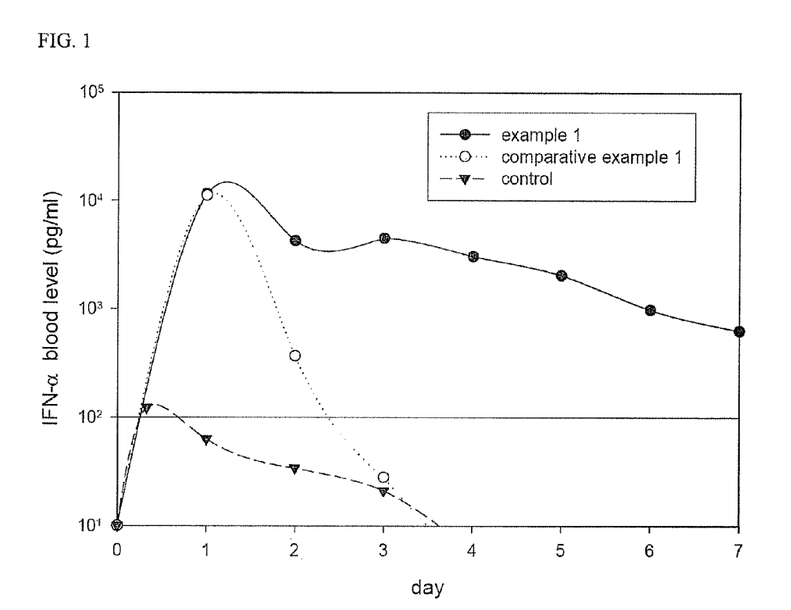
FIG. 1 shows in vivo (rat) release profiles of microparticles of interferon-alpha of Example 1 (-●-), Comparative Example 1 (-○-) and control (-▼-).

The results are shown in FIG. 1.

As shown in FIG. 1, the blood level of interferon-alpha of the rat injected with the dispersion of the microparticles of Example 1 was above $1 \times 10^2$ pg/ml at day 7. The blood level of interferon-alpha of the rat injected with the dispersion of the microparticles of Comparative Example 1 sharply decreased on day 2 and became undetectable on day 4. The control released the most of interferon-alpha on day 1.

EXPERIMENTAL EXAMPLE 2

Sustained Releases of Microparticles of the Invention

Microparticles of interferon-alpha of Example 2 or Comparative Examples 1, 2, or 3 were dispersed into a medium chain triglyceride (Myglyol 812, Sasol) to a concentration of 336 µg IFNα/ml to give injection dispersions.

Each of the microparticle dispersions (0.5 ml) were subcutaneously injected to Sprague Dawley rats (male, 7-8 weeks old). Blood samples were collected once a day for a week. Serum was separated from blood samples and the levels (pg/ml) of interferon-alpha were measured using ELISA. The results are shown in Table 5.

TABLE 5

|  | Day 1 | Day 2 | Day 3 | Day 4 | Day 5 | Day 6 | Day 7 |
|---|---|---|---|---|---|---|---|
| Ex. 2 | 11576 | 2741 | 1707 | 964 | 523 | 300 | 179 |
| C. Ex. 1 | 11250 | 370 | 28 | 4 | ND* | ND | ND |
| C. Ex. 2 | 24466 | 551 | 223 | 81 | 33 | 20 | 11 |
| C. Ex. 3 | 19108 | 689 | 194 | 228 | 66 | 42 | 34 |

*ND = Not Detected.

As shown in Table 5, the blood level of interferon-alpha of the rat injected with the dispersion of the microparticles of Example 2 was above $1 \times 10^2$ pg/ml at day 7. The blood level of interferon-alpha of the rat injected with the dispersion of the microparticles of Comparative Example 1 sharply decreased on day 2 and was below $1 \times 10^2$ pg/ml from day 3.

The blood levels of interferon-alpha in the rat administered with the dispersion of the microparticles of Comparative Example 2, which comprise sodium hyaluronate and an amino acid, without PEG, were maintained above $1 \times 10^2$ pg/ml up to day 3. The blood levels of interferon-alpha in the rat administered with the dispersion of the microparticles of Comparative Example 3, which comprise sodium hyaluronate and PEG, but not an amino acid, were maintained above $1 \times 10^2$ pg/ml for about five (5) days.

EXPERIMENTAL EXAMPLE 3

Effects of the Molecular Weights of PEGs on the Sustained Release

It was evaluated an effect of the molecular weight of PEGs in the microparticles on the sustained release profile of the microparticles.

Microparticles of interferon-alpha of Examples 3, 4 or 5 were dispersed into a medium chain triglyceride (Myglyol 812, Sasol) to a concentration of 336 µg IFNα/ml to give injection dispersions. Each of the microparticle dispersions (0.5 ml) was subcutaneously injected to Sprague Dawley rats (male, 7-8 weeks old). A blood sample was collected on a daily basis for a week. Serum was separated from blood samples and the levels (pg/ml) of interferon-alpha were measured using ELISA. The results are shown in Table 6.

TABLE 6

|  | Day 1 | Day 2 | Day 3 | Day 4 | Day 5 | Day 6 | Day 7 |
|---|---|---|---|---|---|---|---|
| Ex. 3 | 17076 | 854 | 337 | 131 | 74 | 47 | 28 |
| Ex. 4 | 23309 | 3365 | 1306 | 824 | 459 | 266 | 136 |
| Ex. 5 | 16934 | 1101 | 773 | 474 | 252 | 136 | 84 |

As shown in Table 6, the blood level of interferon-alpha of the rat injected with the dispersion of the microparticles of Example 3 was above $1 \times 10^2$ pg/ml up to about day 5. In contrast, the blood levels of interferon-alpha of the rat administered with the dispersion of the microparticles of Examples 4 and 5 were maintained at or above $1 \times 10^2$ pg/ml for 7 days or longer after the administration. The microparticles of Example 4, which comprise PEG 20,000, showed the longest sustained release of interferon-alpha. This indicates that the composition of the present invention shows the most preferred sustained releases of a protein drug when it employs PEG having a molecular weight similar to or substantially same as that of the protein drug.

The results of Table 6 show that the composition produced a longest release of a protein drug when the molecular weight of the polyalkyl oxide is similar to or greater than that of the protein drug, and more preferably about 1:1.

EXPERIMENTAL EXAMPLE 4

Effects of the Amounts of PEGs on the Sustained Release

It was evaluated an effect of the amounts of PEGs in the microparticles on the sustained release profile of the microparticles.

Microparticles of interferon-alpha of Examples 6-10 were dispersed into a medium chain triglyceride (MCT, Myglyol 812, Sasol) to a concentration of 336 µg IFNα/ml to give injection dispersions. Each of the microparticle dispersions (0.5 ml) was subcutaneously injected to Sprague Dawley rats (male, 7-8 weeks old). A blood sample was collected once a day for a week. Serum was separated from blood samples and the levels (pg/ml) of interferon-alpha were measured using ELISA. Table 7 shows the blood levels of interferon-alpha at day 7 ($C_7$) and the amounts of PEGs in the microparticles at the time of injection.

TABLE 7

|  | Ex. 6 | Ex. 7 | Ex. 8 | Ex. 9 | Ex. 10 |
|---|---|---|---|---|---|
| PEG (w/w %) | 4.4 | 7.5 | 10.3 | 14.7 | 18.7 |
| $C_7$(pg/ml) | 14 | 67 | 142 | 194 | 120 |

As shown in Table 7, the blood levels of interferon-alpha of the rat, at day 7, were above $1 \times 10^2$ pg/ml, when the contents of the PEG in the microparticles were about 10% (w/w) or more.

EXPERIMENTAL EXAMPLE 5

Effects of the Types of Amino Acids

This experiment tests the effects of the types of amino acids contained in the microparticles of the present invention on the sustained release.

Microparticles of interferon-alpha of Examples 11-14 were dispersed into a medium chain triglyceride (MCT, Myglyol 812, Sasol) to a concentration of 336 µg IFNα/ml to give injection dispersions. Each of the microparticle dispersions (0.5 ml) was subcutaneously injected to Sprague Dawley rats (male, 7-8 weeks old). A blood sample was collected once a day for a week. Serum was separated from blood samples and the levels (pg/ml) of interferon-alpha were measured using ELISA. Table 8 shows blood levels of interferon-alpha at day 7 ($C_7$).

TABLE 8

|  | Example 11 | Example 12 | Example 13 | Example 14 |
|---|---|---|---|---|
| Amino acids | Histidine | Aspartic acid | Threonine | Methionine |
| $C_7$ (pg/ml) | 236 | 208 | 13 | 115 |

As can be seen from Table 8, the rats administered with the dispersions of microparticles comprising histidine, aspartic acid, or methionine maintained its blood level of interferon-alpha above $1 \times 10^2$ pg/ml, at days 1-7. The blood level of the rat injected with the dispersion of the microparticles comprising threonine was about 13 pg/ml of interferon-alpha at day 7. Threonine is highly water-soluble. It is speculated that microparticles containing threonine fast absorb body fluids in the body of the subject and release an interferon-alpha faster, compared to those containing hydrophobic amino acids such as histidine, aspartic acid or methionine.

EXPERIMENTAL EXAMPLE 6

Microparticles of Interferon-alpha With or without Lecithin

This experiment tests the effects of an excipient (lecithin) contained in the microparticles of the present invention on the sustained release of interferon-alpha.

Microparticles of interferon-alpha of Examples 15-19 were dispersed into a medium chain triglyceride (MCT, Myglyol 812, Sasol) to a concentration of 336 µg IFNα/ml to give injection dispersions. Each of the microparticle dispersions (0.5 ml) was subcutaneously injected to Sprague Dawley rats (male, 7-8 weeks old). A blood sample was collected once a day for a week. Serum was separated from blood samples and the levels (pg/ml) of interferon-alpha were measured using ELISA. Table 9 shows blood levels of interferon-alpha at day 7 ($C_7$).

TABLE 9

|  | Example 15 | Example 16 | Example 17 | Example 18 | Example 19 |
|---|---|---|---|---|---|
| $C_7$ (pg/ml) | 253 | 518 | 136 | 120 | 128 |

All of the dispersions of Examples 15-19 comprise an amino acid in an amount of 30% by weight or more in the microparticles. As can be seen from Table 9, all dispersions tested released the interferon-alpha at a concentration higher than $1 \times 10^2$ pg/ml at day 7. Interestingly, the dispersions of Examples 15 and 16, which do not contain lecithin, released a greater amount of the interferon-alpha than the dispersions of Examples 17-19, which contain lecithin, at day 7.

EXPERIMENTAL EXAMPLE 7

Microparticles of Erythropoietin

The sustained release of erythropoietin of the microparticles of the present invention was tested.

Microparticles of erythropoietin of Example 20 were dispersed into a medium chain triglyceride (MCT, Myglyol 812, Sasol) to a concentration of 85 µg EPO/ml to give injection dispersions. Each of the microparticle dispersions (0.5 ml) was subcutaneously injected to Sprague Dawley rats (male, 7-8 weeks old). A blood sample was collected once a day for a week. Serum was separated from blood samples and the levels (mIU/ml) of erythropoietin were measured using ELISA (Catalog #DEP00, R&D Systems, The ELISA Guidebook, Humana Press, John R. Crowther, 2001). The results are shown in FIG. 2.

Figure 2:
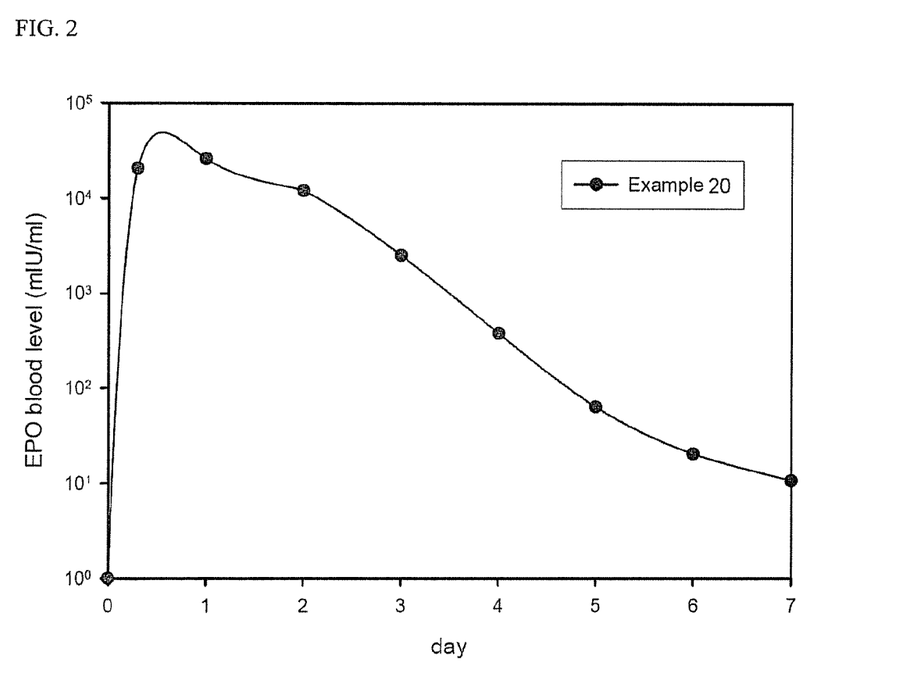
FIG. 2 shows an in vivo release profile of microparticles of erythropoietin of Example 20.

The results in FIG. 2 indicate that the compositions of the present invention effectively produce a sustained release for more than 7 days when applied to erythropoietin.

EXPERIMENTAL EXAMPLE 8

Microparticles of FSH

The sustained release of FSH of the microparticles of the present invention was tested.

Microparticles of follicle stimulating hormone (FSH) of Example 21 were dispersed into a medium chain triglyceride (MCT, Myglyol 812, Sasol) to a concentration of 53 µg FSH/ml to give injection dispersions. Each of the microparticle dispersions (0.5 ml) was subcutaneously injected to Sprague Dawley rats (male, 7-8 weeks old). A blood sample was collected once a day for a week. Serum was separated from blood samples and the levels (mIU/ml) of FSH were measured using ELISA (ELISA, catalog #RE52121, IBL, The ELISA Guidebook, Humana Press, John R. Crowther, 2001). The results are shown in FIG. 3.

Figure 3:
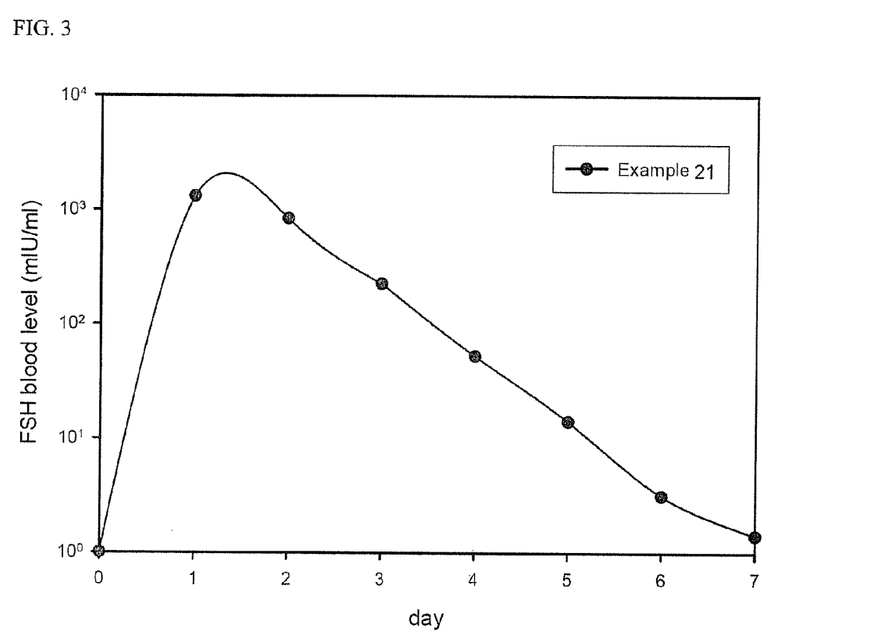
FIG. 3 shows an in vivo release profile of microparticles of FSH of Example 21.

As can be seen from FIG. 3, the FSH was detected in the rats at day 7.

EXPERIMENTAL EXAMPLE 9

Microparticles of Interferon-alpha

Microparticles of interferon-alpha were tested for their sustained release of interferon-alpha by using a monkey. Microparticles of interferon-alpha of Example 1 were dispersed into a medium chain triglyceride (MCT, Myglyol 812, Sasol) to a concentration of 110 µg IFNα/ml to give injection dispersions.

Figure 6:
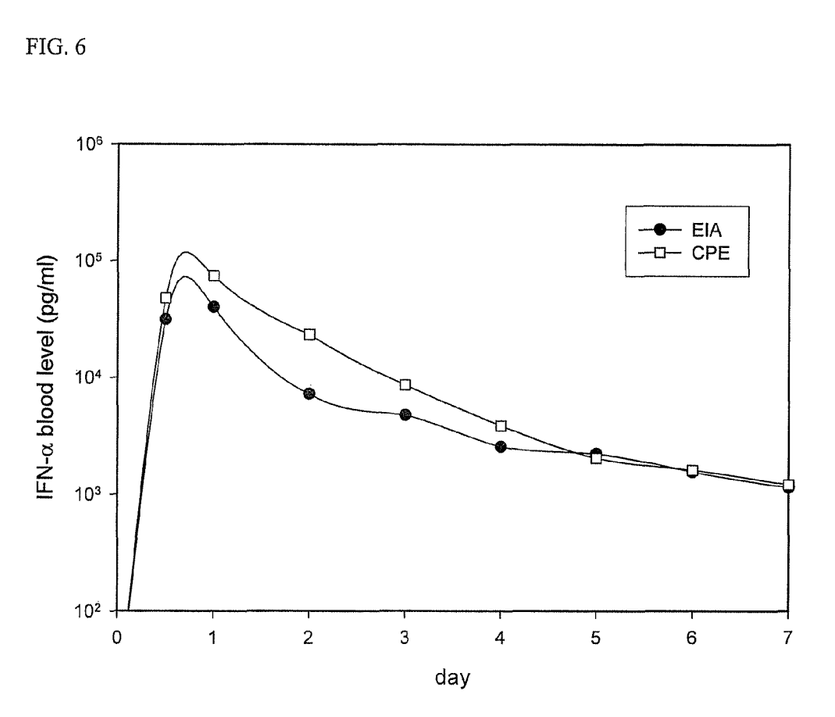
FIG. 6 shows an in vivo (in monkey) release profile of microparticles of interferon-alpha of Example 1, as measured by ELISA (-●-) and CPE (-□-).

The microparticle dispersion (1.5 ml) was subcutaneously injected to Cynomolgus Monkey (male). A blood sample was collected once a day for a week. Serum was separated from blood samples and the blood levels (pg/ml) of interferon-alpha were measured using CPE (Cytopathic Effect Inhibition) Assay and ELISA (High Sensitivity IFN-alpha ELISA System (Amersham, RPN2789), The ELISA Guidebook, Humana Press, John R. Crowther, 2001). The blood levels of interferon-alpha at days 5, 6 and 7 ($C_5$, $C_6$ and $C_7$, respectively) were shown in Table 10 and FIG. 6.

TABLE 10

| | $C_5$ | $C_6$ | $C_7$ |
|---|---|---|---|
| CPE (pg/ml) | 2047.8 | 1618.1 | 1216.1 |
| ELISA (pg/ml) | 2227.6 | 1564.1 | 1153.0 |

The CPE is an assay to measure protein activity. A cell line MDBK is killed by the attack of VSV (Vesicular Stomatitis Virus). This phenomenon is called "cytopathic effect." The cytopathic effect is inhibited, i.e., the cell is protected from the lethal attack of virus, when the cell contains interferon-alpha at the time the virus attacks the cell. The physiological activity of interferon-alpha can be determined by measuring the inhibition.

MDBK cells were cultivated in a 96 well microtiter plate for 24 hours. Diluted solutions of interferon-alpha at predetermined concentrations were added to the wells and a cultivation was performed for 24 hours. Wells were washed with D-PBS to remove the interferon-alpha and received VSV. The cells were further grown and stained, followed by a measurement of their optical density (OD). European Pharmacopoeia "Interferon Alfa-2 Concentrated Solution" pp 1812~1815, 2005, Journal of Virology, 37(2), pp 755-758 (1981).

As shown in Table 10, the ELISA shows that the blood level of interferon-alpha were maintained above 100 pg/ml at days 5, 6 and 7. The CPE results, which are substantially same to those of the ELISA results, indicate that the interferon-alpha in the body of monkey maintain its physiological activity at day 7. The results show that the composition of the present invention produced sustained releases of physiologically active interferon-alpha for an extended period of time, e.g., 7 days and beyond. Therefore, the sustained release composition of interferon-alpha according to the present invention is suitable for 7-day sustained release interferon-alpha formulations.

EXPERIMENTAL EXAMPLE 10

Sustained Release of Erythropoietin

Microparticles of erythropoietin of Example 22 were dispersed into a medium chain triglyceride (MCT, Myglyol 812, Sasol) to a concentration of 336 µg EPO/ml to produce an injection dispersion.

The dispersion (0.5 ml) was subcutaneously injected to Sprague Dawley rats (male, 7-8 weeks old). A blood sample was collected once a day for a week. Serum was separated from blood samples and the levels (mIU/ml) of erythropoietin were measured using ELISA (Catalog #DEP00, R&D Systems, The ELISA Guidebook, Humana Press, John R. Crowther, 2001). The results are shown in FIG. 4.

Figure 4:
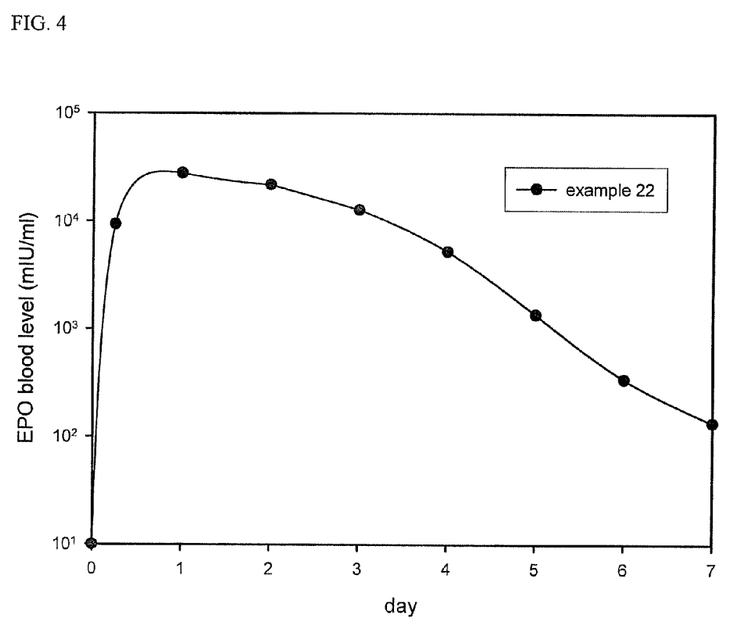
FIG. 4 shows an in vivo release profile of microparticles of erythropoietin of Example 22.

The results in FIG. 4 indicate that the compositions of the present invention are suitable for use in sustained release formulations of erythropoietin.

EXPERIMENTAL EXAMPLE 11

Sustained Release of FSH

A sustained release of a composition containing FSH, according to the present invention, was determined in rats.

Microparticles of FSH of Example 23 were dispersed into a medium chain triglyceride (Myglyol 812, Sasol) to a concentration of 336 µg FSH/ml to produce an injection dispersion. The dispersion (0.5 ml) was subcutaneously injected to rats (Sprague Dawley Rat, male, 7-8 weeks). A blood sample was collected once a day for a week. Serum was separated from blood samples and the levels (mIU/ml) of FSH were measured using ELISA (Catalog #RE52121, IBL, The ELISA Guidebook, Humana Press, John R. Crowther, 2001). The results are shown in FIG. 5.

Figure 5:
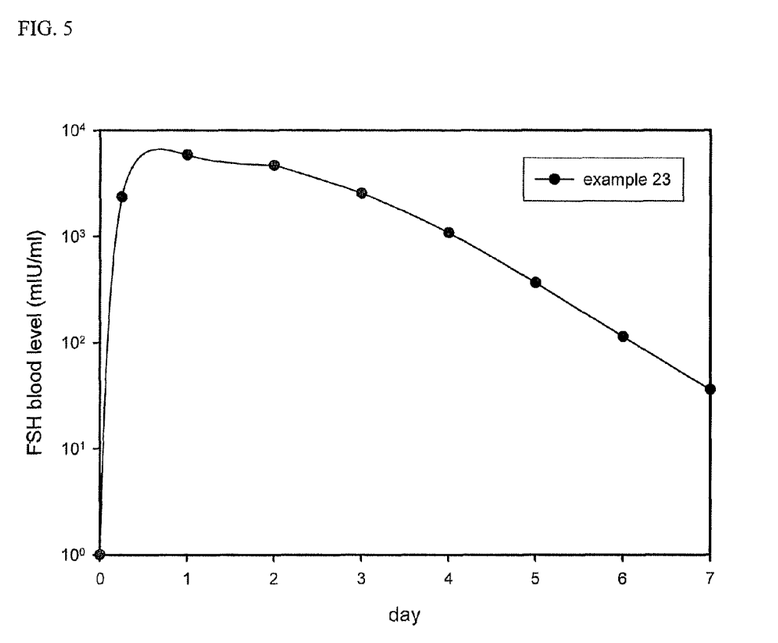
FIG. 5 shows an in vivo release profile of microparticles of FSH of Example 23.

The results in FIG. 5 indicate that the compositions of the present invention are suitable for use is sustained release formulations of FSH.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A sustained release composition comprising
a carrier substrate and
a protein drug incorporated into the carrier substrate,
said carrier substrate comprising
(a) a hyaluronic acid or its salt, having a molecular weight of at least 3,000,000 Da,
(b) a polyalkyl oxide, and
(c) an amino acid wherein the amino acid is selected from the group consisting of aspartic acid, histidine, isoleucine, leucine, methionine, valine and a combination or at least two of the foregoing amino acids,
wherein a ratio of a molecular weight (Da) of the protein drug to a molecular weight (Da) of the polyalkyl oxide is about 1:0.5-1:1.8

2. The composition according to claim 1, wherein a total amount of the hyaluronic acid or its salt, the polyalkyl oxide and the amino acid is about 50-99.95% by weight based on dry weight of the composition.

3. The composition according to claim 2, wherein the total amount of the hyaluronic acid or its salt, the polyalkyl oxide and the amino acid is about 70-99.95% by weight based on dry weight of the composition.

4. The composition according to claim 1, wherein the polyalkyl oxide is a polyethylene glycol, a polypropylene glycol, a copolymer thereof, or a mixture thereof.

5. The composition according to claim 4, wherein the polyalkyl oxide is a polyethylene glycol.

6. The composition according to claim 5, wherein the polyalkyl oxide has a molecular weight of at least 1,000 Da.

7. The composition according to claim 1, wherein the protein drug is an interferon, erythropoietin, or a follicle stimulating hormone.

8. The composition according to claim 1, which further comprises a stabilizer.

9. The composition according to claim 1, wherein the ratio of the molecular weight (Da) of the protein drug to the molecular weight (Da) of the polyalkyl oxide is about 1:1.

10. The composition according to claim 1, which is formulated into microparticles, pellets, rods, filaments, cylinders, or films.

11. A pharmaceutical formulation for injection, which comprises the composition according to claim 1 dispersed in an injection medium.

12. The pharmaceutical formulation according to claim 11, wherein the injection medium is selected from the group consisting of distilled water; a buffer; corn oil, sesame oil, cotton seed oil, soybean oil, peanut oil, mono-glyceride, di-glyceride, tri-glyceride, mineral oil, squalene, and mixtures thereof.

13. An aerosol formulation comprising the composition according to claim 1.

14. A sustained release composition comprising
a carrier substrate and
a protein drug incorporated into the carrier substrate,
said carrier substrate being comprising
- (a) a hyaluronic acid or its salt having molecular weight of at least 3,000,000 Da,
- (b) a polyethylene glycol, and
- (c) an amino acid selected from the group consisting of aspartic acid, histidine, isoleucine, leucine, methionine, valine, and a combination of at least two of the foregoing amino acids, wherein a ratio of a molecular weight (Da) of the protein drug to a molecular weight (Da) of the polyethylene glycol is about 1:0.8-1:1.8 and the molecular weight of the polyethylene glycol is at least 1,000 Da.

15. The composition according to claim 1, wherein the protein drug is contained in an amount of 0.05-5% by weight based on a dry weight of the composition.

16. The composition according to claim 1, wherein the hyaluronic acid or its salts is contained in an amount of 20-50% by weight based on a dry weight of the composition.

17. The composition according to claim 1, wherein the polyalkyl oxide is contained in an amount of 5-60% by weight based on a dry weight of the composition.

18. The composition according to claim 1, wherein the amino acid is contained in an amount of 10-80% by weight based on a dry weight of the composition.

19. The composition according to claim 1, wherein the amino acid is selected from the group consisting of aspartic acid, histidine, isoleucine, leucine, methionine, and a combination of at least two of the foregoing amino acids.

* * * * *